United States Patent [19]

Janick et al.

[11] 4,426,808

[45] Jan. 24, 1984

[54] METHOD OF NON-AGRICULTURAL PRODUCTION OF JOJOBA WAX

[75] Inventors: Jules Janick, West Lafayette, Ind.; Daniel C. Wright, Hornell, N.Y.

[73] Assignee: Purdue Research Foundation, West Lafayette, Ind.

[21] Appl. No.: 466,877

[22] Filed: Feb. 16, 1983

Related U.S. Application Data

[63] Continuation of Ser. No. 266,322, May 22, 1981, abandoned.

[51] Int. Cl.³ .............................................. A01G 1/00
[52] U.S. Cl. ...................................................... 47/58
[58] Field of Search ............................................ 47/58

[56] References Cited

U.S. PATENT DOCUMENTS 4,204,366  5/1980  Janick et al. ............................. 47/58
4,241,536  12/1980  Saint-Firmin ........................... 47/58
4,291,498  9/1981  Janick et al. ............................. 47/58
4,301,619  11/1981  Janick et al. ............................. 47/58

FOREIGN PATENT DOCUMENTS 1387821  3/1975  United Kingdom .................... 47/58

OTHER PUBLICATIONS

Tissue Culture of Jojoba and Guayule, Huang & Murashige, 32nd Ann. Mtg. Tissue Culture Assoc., Wash. D. C., Jun. 1981.

Primary Examiner—Robert E. Bagwill
Attorney, Agent, or Firm—John R. Nesbitt

[57] ABSTRACT

This invention relates to a method for the non-agricultural production of jojoba wax through the culture of asexual embryos of jojoba.

4 Claims, 2 Drawing Figures

METHOD OF NON-AGRICULTURAL PRODUCTION OF JOJOBA WAX

RELATED INVENTION

This application is a continuation of my co-pending United States patent application Ser. No. 06/266,322 filed May 22, 1981 (now abandoned).

FIELD OF THE INVENTION

This invention relates to culture of living plant tissue to produce embryos of jojoba.

BACKGROUND OF THE INVENTION

U.S. Pat. No. 4,204,366, teaches a method whereby asexual embryos of cacao (*Theobroma cacao* L.) can be proliferated in vitro to produce useful products, i.e. a cocoa-butter like product. This invention covers a non-agricultural method for producing jojoba wax by tissue culture procedures. In this invention we describe a new system to produce jojoba wax, a wax ester of long chain (20–22 carbon) fatty acids and alcohols produced by the jojoba shrub [*Simmondsia chinensis* (Link)], which has useful properties as an industrial lubricant.

THE DRAWINGS

FIG. 1 is a graphic representation of the results of a gas chromatographic separation of commercial jojoba oil. Identification of peaks is based on known jojoba wax ester composition. The parameters used in the graph are

| | |
|---|---|
| column | 330° C. |
| detector | 400° C. |
| injector | 300° C. |
| chart speed | 0.5 cm/sec |
| attenuation | 128 |
| carrier gas | 30 ml/min |
| 3% OV-1 2 m × 2 mm | stainless steel column |

FIG. 2 is a graphic representation of the results of a gas chromatographic separation of wax esters of asexual embryos of jojoba. Identification is based on retention times from FIG. 1. The parameters used in the graph are

| | |
|---|---|
| column | 330° C. |
| detector | 400° C. |
| injector | 300° C. |
| chart speed | 0.5 cm/sec |
| attenuation | 128 |
| carrier gas | 30 ml/min |
| 3% OV-1 2 m × 2 mm | stainless steel column |

DETAILED DESCRIPTION OF THE INVENTION

In order to obtain zygotic embryos for further growth and proliferation, a group of immature jojoba fruits are selected and individually cut open and the developing immature zygotic embryos are separated out of each fruit. Zygotic embryos of less than about twenty milligrams by weight are separated out and discarded and none in excess of one hundred milligrams by weight are retained. The zygotic embryos selected as aforesaid, namely those ranging anywhere from twenty milligrams to one hundred milligrams in weight, are then placed on the basal medium described below.

The zygotic embryos are then placed on said basal medium and grown thereupon, and eventually they will produce asexual embryos.

The maturing asexual embryos each form two cotyledons, thereby resembling a normal seed, but without a seed coat. As the asexual embryos continue to grow, some will eventuate in plant production (and these are discarded) and some grow out to what nearly resemble "coatless" seeds, and it is these embryos that are used for wax production.

Immature fruits of jojoba undergo a process of asexual embryogenesis when cultured on a basal medium consisting of salts as described in a paper by Toshio Murashige and Folke Skoog (1962) entitled *A revised medium for rapid growth and bioassays with tissue cultures*. Physiol. Plant. 15:473–497.

The pecise formulation is as follows:

| Components | mg/liter |
|---|---|
| Salts[1] | |
| $NH_4NO_3$ | 1650 |
| $KNO_3$ | 1900 |
| $CaCl_2.2H_2O$ | 440 |
| $MgSO_4.7H_2O$ | 370 |
| $KH_2PO_4$ | 170 |
| Na.EDTA | 373 |
| $FeSO_4.7H_2O$ | 27.8 |
| KI | 0.83 |
| $H_3BO_3$ | 6.2 |
| $MnSO_4.7H_2O$ | 22.3 |
| $ZnSO_4.7H_2O$ | 8.6 |
| $Na_2MoO_4.2H_2O$ | 0.25 |
| $CuSO_4.5H_2O$ | 0.025 |
| $CaCl_2.6H_2O$ | 0.025 |

The formulation described above is commonly referred to by those skilled in the art as "Murashige and Skoog salts".

The asexual embryos continue to proliferate in culture, mature to a seed-like state, and are capable of germination.

Figure 1:
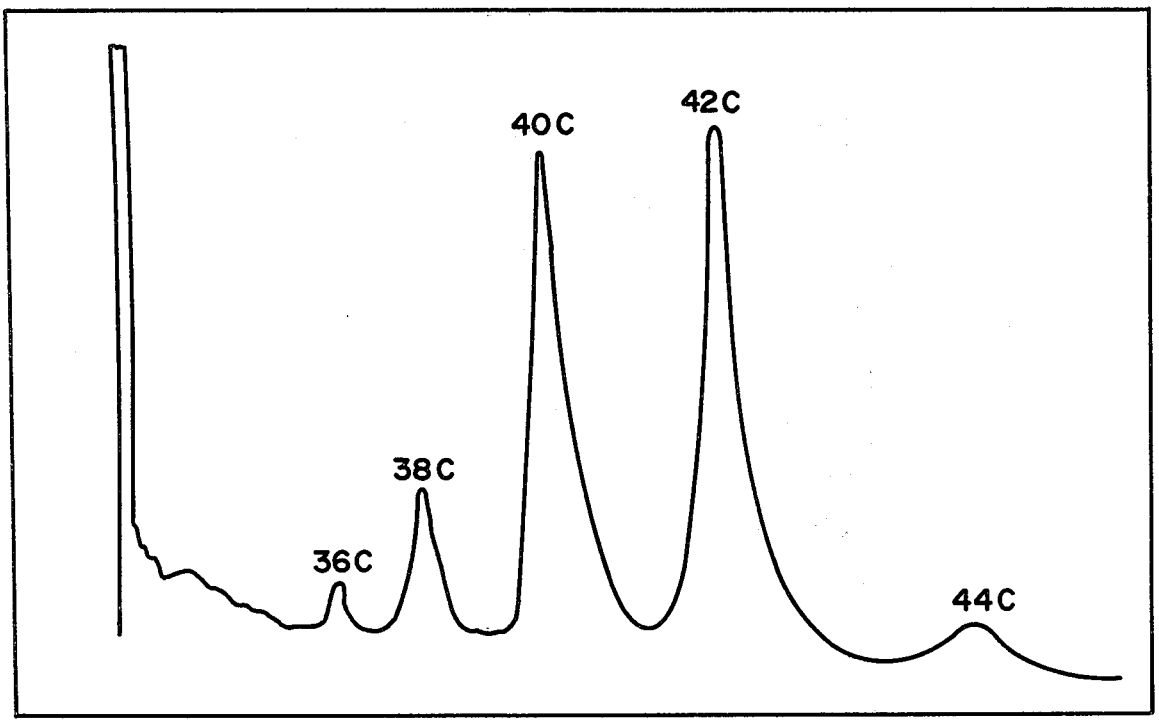
Figure 2:
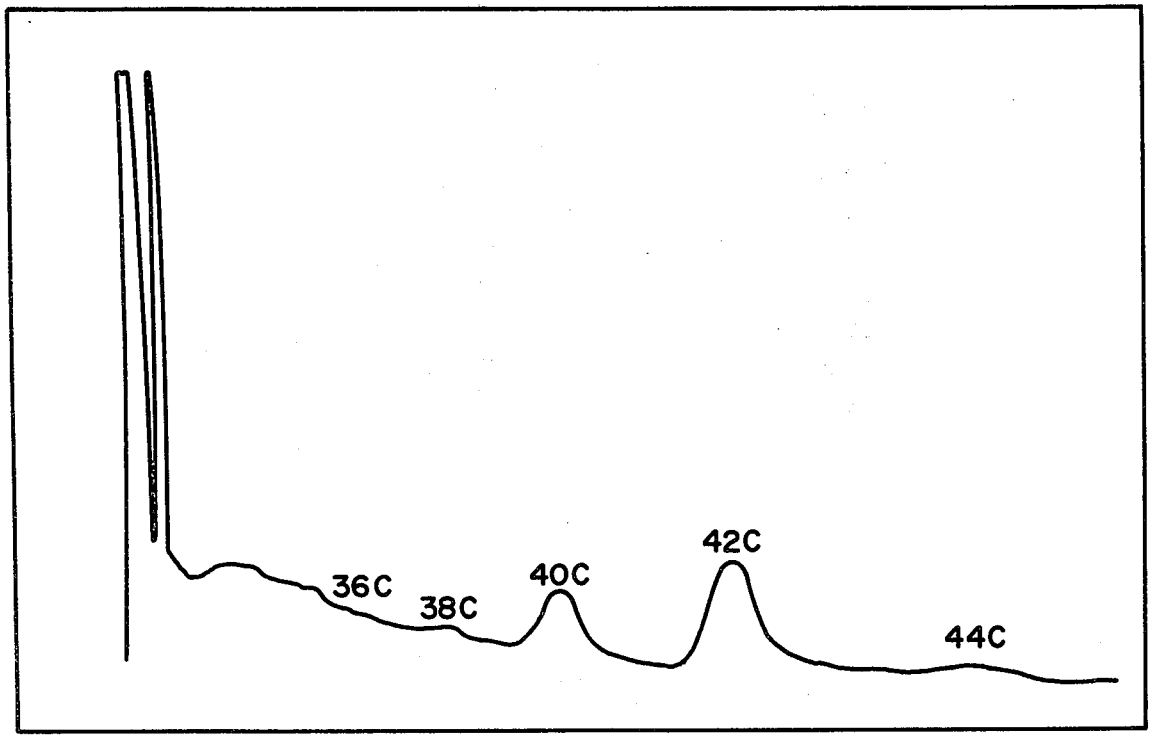

Analysis of lipids for asexual embryos have shown the presence of wax esters of long chain fatty acids and alcohols that are identical with commercial jojoba wax as measured by gas-liquid chromatography. The chromatograph tracing of the wax esters from commercial jojoba wax and asexual embryos of jojoba are shown in FIGS. 1 and 2. These results are supported by the data shown in Table 1 as follows:

TABLE 1

| | | Gas Chromatographic Analysis of Asexual Embryo Lipids as Compared to Jojoba Oil | | | | | | |
|---|---|---|---|---|---|---|---|---|
| Source of wax | | Ester Carbon Length | | | | | | |
| | | 36 | 38 | 40 | 42 | 44 | Total | % wax |
| Jojoba Oil | Area[1] | 376 | 2059 | 9927 | 15025 | 280 | 27668 | 100% |
| | Area % | 1.4 | 7.4 | 35.9 | 54.3 | 1.0 | | |
| Asexual | Area | tr | tr | 975 | 2766 | tr | 3742 | 13.5 |

TABLE 1-continued

Gas Chromatographic Analysis of Asexual
Embryo Lipids as Compared to Jojoba Oil

| Source of wax | | Ester Carbon Length | | | | | Total % wax |
|---|---|---|---|---|---|---|---|
| | | 36 | 38 | 40 | 42 | 44 | |
| Embryo[2] | Area % | <0.1 | <0.1 | 26.1 | 73.9 | <0.1 | |

[1]Determined by Hewlett Packard 3880 S Integrator/1000
[2]2.46 g fresh weight, 0.33 g dry weight, 32.4 mg lipid, 9.8% lipid In a subsequent study initialed in May 1982, zygotic asexual embryos of jojoba, each between the size of 20 and 100 mg, were cultured on the identical basal medium previously described with various concentrations of 2,4-dichlorophenoxyacetic acid (2,4-D). The results indicate that asexual embryogenesis was stimulated by the addition of 1 mg/liter 2,4-D as shown in Table 2 below:

TABLE 2

The effects of 2,4-dichlorophenoxyacetic acid on the induction of asexual embryogensis in zygotic embryos of jojoba.

| 2,4-D (mg/liter) | No. cultures | Cultures with asexual embryos | |
|---|---|---|---|
| | | No. | % |
| 0 | 60 | 0 | 0 |
| 0.1 | 60 | 0 | 0 |
| 1 | 60 | 9 | 15 |
| 10 | 60 | 0 | 0 |

CONCLUSION

These results demonstrate that immature asexual embryos of *Simmondsia chinesis* can be induced to proliferate asexual embryos and that these asexual embryos will produce wax esters in tissue culture similar to the wax esters produced by jojoba under normal field culture.

We claim:

1. A non-agricultural method for the production of embryos of *Simmondsia chinensis* consisting of the steps of:
    selection and excision of immature zygotic embryos of jojoba from immature jojoba fruits, said selection being made from the group of zygotic embryos excised aforesaid, and none being retained for proliferation in excess of one hundred milligrams by weight;
    Proliferation of immature zygotic embryos of jojoba in a basal medium;
    Growing asexual embryos in a basal medium; and
    Harvesting asexual embryos and extracting the liquid wax.

2. Asexual embryos capable of producing wax esters typical of jojoba under tissue culture conditions.

3. The method of claim 1 wherein the proliferation step is stimulated by the addition of 2,4-dichlorophenoxyacetic acid.

4. The method according to claim 3 wherein proliferation is best accomplished with concentration of 2,4-D of about 1 mg/liter.

* * * * *